United States Patent

Shigematsu et al.

[11] Patent Number: 5,829,433
[45] Date of Patent: Nov. 3, 1998

[54] INHALATION VALVE

[75] Inventors: Nobuo Shigematsu, Tokyo; Kenichi Ono; Tsutomu Watabe, both of Iwatsuki, all of Japan

[73] Assignee: Shigermatsu Works Co., Ltd., Tokyo, Japan

[21] Appl. No.: 673,944

[22] Filed: Jul. 1, 1996

[30] Foreign Application Priority Data

Jun. 30, 1995 [JP] Japan ................................... 7-186532

[51] Int. Cl.⁶ ................................................ A61M 16/00
[52] U.S. Cl. ................................ 128/202.28; 128/203.11; 128/205.24
[58] Field of Search ...................... 128/202.28, 202.29, 128/203.11, 205.24

[56] References Cited

U.S. PATENT DOCUMENTS

| 3,626,936 | 12/1971 | Barker | 128/203.11 |
| 4,819,628 | 4/1989 | Eisenberg et al. | 128/203.11 |
| 5,005,568 | 4/1991 | Loescher et al. | 128/203.11 |
| 5,088,485 | 2/1992 | Schock | 128/203.11 |
| 5,119,809 | 6/1992 | Gerson | 128/203.11 |
| 5,127,397 | 7/1992 | Kohnke | 128/203.11 |
| 5,355,877 | 10/1994 | Cheng | 128/203.11 |

*Primary Examiner*—Aaron J. Lewis
*Attorney, Agent, or Firm*—Sherman and Shalloway

[57] ABSTRACT

Film made of floppy and deformable synthetic resin is used as a valve body of an inhalation valve and attached to the surface of a valve seat which is formed to a concave groove like shape having an arbitarily sectional view. The said valve body can not be applied to a conventional valve seat which has a flat surface. The inhalation valve is embedded to the breathing-in space of mask in which a filter pad is put in and prevent the valve body which separates from the seat at inhalation timing from entering into face contact part.

8 Claims, 5 Drawing Sheets

INHALATION VALVE

BACKGROUND OF THE INVENTION

This invention relates to an inhalation valve which is opened by pressure falling due to the breathing-in action, particularly, relates to an inhalation valve used for a breathing protective mask.

DESCRIPTION OF THE PRIOR ART

The inhalation valve characterized by installing disk shape thin film valve body made of rubber or the like to the seat located at the center of the valve and the said thin film valve body is always (while not operated) attached to the seat by keeping flat and disk shape so as to close the valve is well-known.

The conventionally well-known inhalation valve has the following defect. That is, since it is needed that the thin film valve body to have adequate hardness and thickness to maintain the necessary shape by itself, and consequently, corresponding power to open the thin film valve body is required, there is a limitation for the reduction of inhalation resistance (lower inhalation resistance promises easy breathing).

SUMMARY OF THE INVENTION

The object of this invention is to provide an inhalation valve of which inhalation resistance is remarkably lower than that of the well-known inhalation valve, and also to provide a mask of which inhalation resistance is remarkably lower than that of the well-known mask. And another object of this invention is to provide a lower profile mask, that is, the distance from a face to an outer surface of the mask is shorter when it is worn, and also to provide a mask having a wider range of view.

A seat is formed to a concave groove shape having an arbitrarily sectional view, and a film valve body made of film sheet is curved like U figure and is attached to the said seat which has concave groove shape. By using this structure, it becomes possible to use a valve body made of very thin plastic film which can not be applied to the conventionally well-known structure of valve, and consequently the inhalation resistance of the inhalation valve is remarkably reduced. The inhalation valve which has the said structure is embedded to a breathing-in space of mask so as to arrange the valve body of the inhalation valve not rising by itself and not entering into a face contact portion. Also sticking out of the mask from a face is minimized by designing a distance between face and a face contact part of mask as short as possible.

Figure 1:
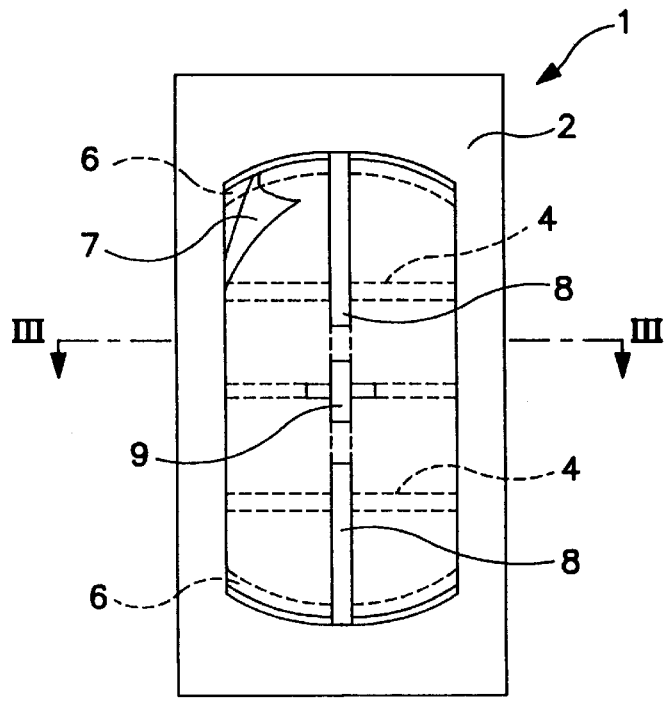
FIG. 1 An elevational view from an inhalation side of one example of an inhalation valve of this invention FIG. 2 A left side elevational view of FIG. 1

Illustration of numerical mark
1: inhalation valve
2: seat body
3: back bone
4: rib
5: end wall
6: valve body supporting surface
7: film valve body
8: valve body floating preventive stick
9: film valve body holding projection
10: cross shaped hole
11: face contact part
12: main body of breathing-in space
13: cover of breathing-in space
14: filter pad
15: projection
16: projection
21: face contact part
22: main body of breathing-in space
23: cover of breathing-in space
24: filter pad
25: inhalation valve
26: round thin film valve body

DETAILED DESCRIPTION OF THE INVENTION

The above and further objects and novel features of this invention will more fully appear from the following detailed description when the same is read in connection with the accompanied drawings. It is to be expressly understood, however, that the drawings are for the purpose of illustration only and are not intended as a definition of the invention.

Figure 2:
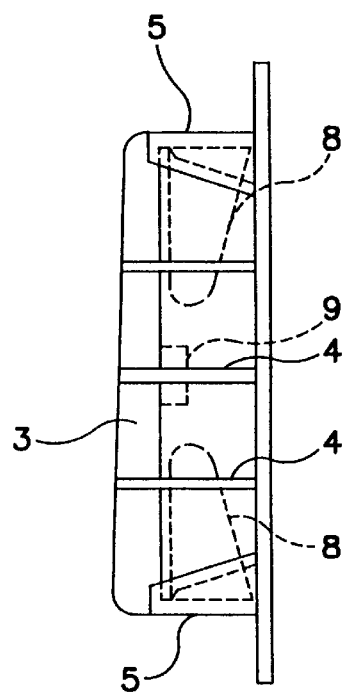
Figure 3:
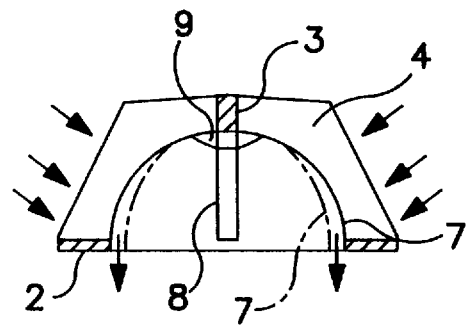
FIG. 3 A III—III line cross sectional view of FIG. 1
Figure 4:
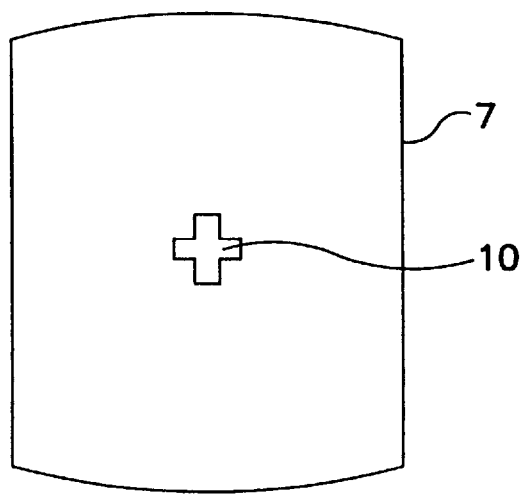
FIG. 4 A plane view of a film valve body removed from the inhalation valve illustrated in FIG. 1, 2 and 3

FIG. 1 is an elevational view from breathing-in side of an inhalation valve of one Example of this invention (in the drawing, to make the existence of a film valve body clear, end part of film valve body is partially separated from surface of a seat). FIG. 2 is a left side elevational view of FIG. 1, FIG. 3 is a III—III line cross sectional view of FIG. 1 and FIG. 4 is a plane view of a film valve body removed from the inhalation valve illustrated in FIG. 1, 2 and 3. In these drawings, 1 indicates an inhalation valve. A seat 2 is composed by one back bone 3, three ribs 4 and a valve body supported surface 6 which is arranged at a pair of end wall 5, and a film valve body 7 is formed like U figure and closely attached to the attaching surface by using a self recovering force which film valve body originally has. In the drawings, 8 indicates a stick to prevent floating of a valve body which is projected from the each end wall 5 forwarding to the surface of seat of back bone position, 9 is a cross shaped projection arranged at the center of the surface of seat of back bone position to hold a film valve body 7. The cross shaped hole 10 bored in the center of the film valve body is fit into the projection holder 9, and the film valve body is attached closely to the groove shaped seat of semicircular cross sectional view under the influence of a self recovering force of film valve body. During the breathing action, as illustrated by dotted line in FIG. 3, the film valve body is removed from the seat, open the breathing-in opening and make inflow air or other gases to the inhalation side at every inhalation. The valve body floating preventive stick 8 prevents the floating of the film valve body 7 during the action. And, generally, as the material of film valve body, synthetic resin film of 20–80 micron thickness which has sufficient recovery force to the original flat shape is used.

Figure 5:
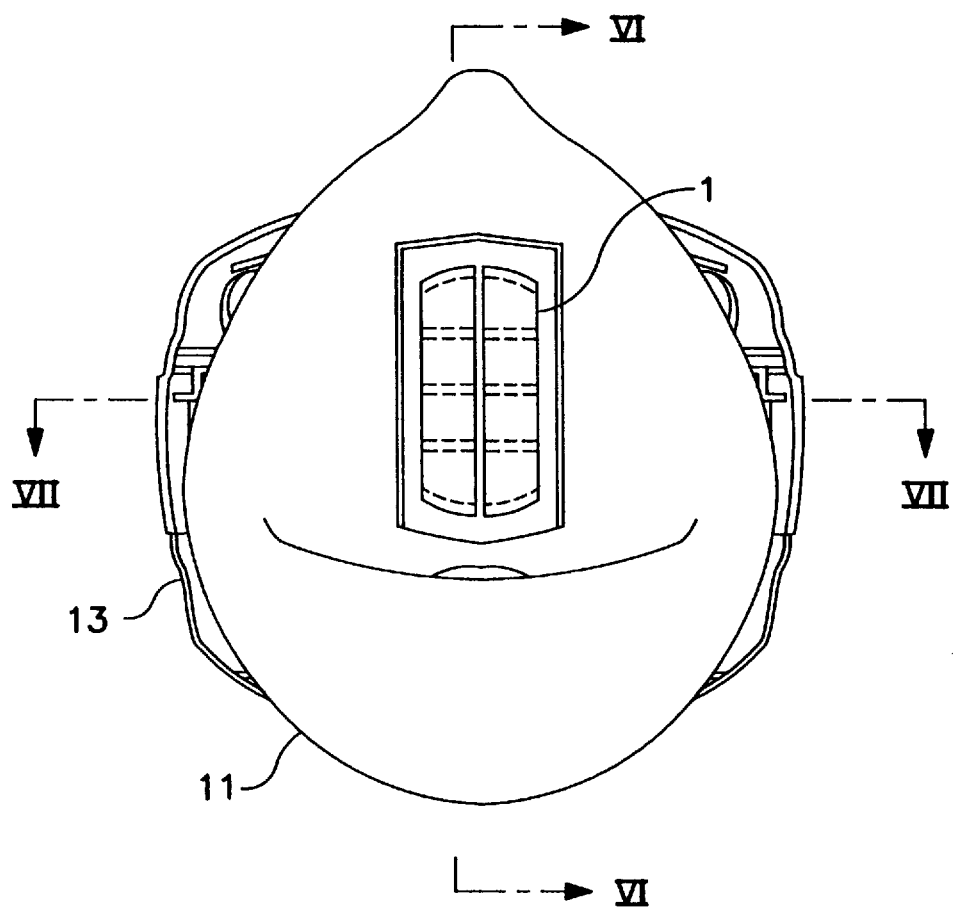
FIG. 5 A rear elevational view of one example of a dust mask wherein a fastening band is abbreviated FIG. 6 A VI—VI line cross sectional view of FIG. 5
Figure 6:
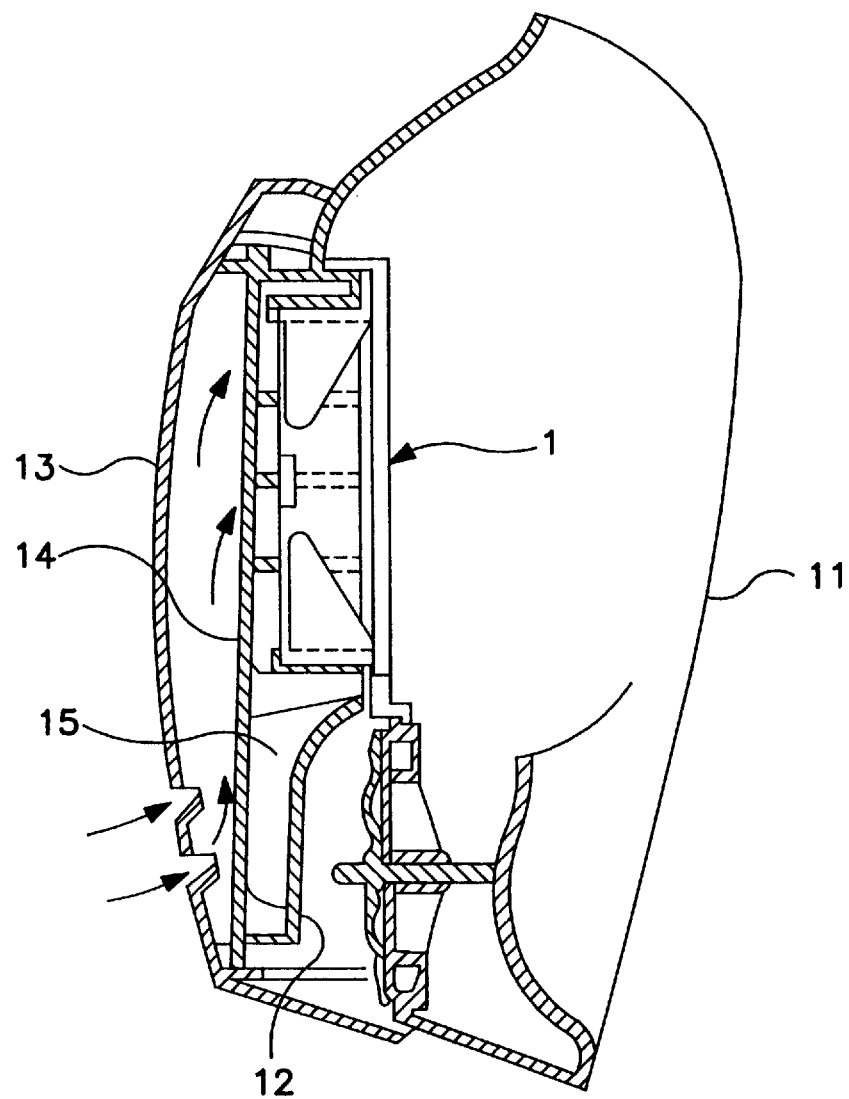
Figure 7:
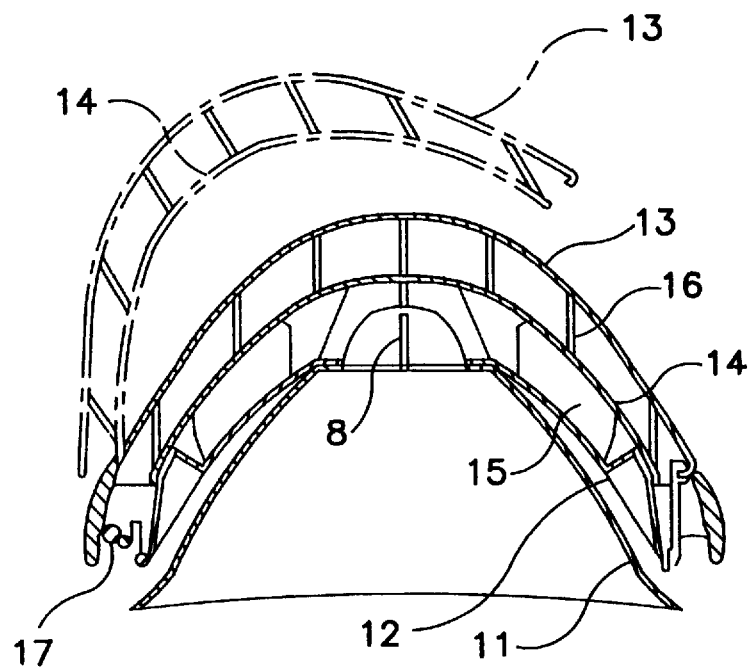
FIG. 7 A VII—VII line cross sectional view of FIG. 5

FIG. 5 is a rear elevational view of one Example of a dust mask of this invention illustrated in FIG. 1, 2 and 3, wherein a fastening band is abbreviated. FIG. 6 is a VI—VI line cross sectional view of FIG. 5, and FIG. 7 is a VII—VII cross sectional view of FIG. 5. In the drawings, 11 indicates a face contact part made of synthetic resin which has adequate pliability and elasticity, 12 indicates a main body of breathing-in space made of synthetic resin or the like installed to face contact part 11, 13 indicates a cover of breathing-in space made of synthetic resin and 14 indicates a filter pad made of non-woven cloth or the like. The filter pad 14 is held between multiple projections 15 formed on the inner surface of the main body of breathing-in space and multiple projections 16 formed on the inner surface of the cover of breathing-in space. And the said multiple projections are formed by one time molding method. The cover of breathing-in space 13 is installed to one side of the main body of breathing-in space 12 by means of axis 17 as to allow flexible turning, and can be opened at the position indicated by dotted line in FIG. 7 and permit an easily exchange of filter sheet as occasion demands. At the actual use of the mask, air for breathing is breathed in from an oblong hole bored in lower position of the cover of breathing-in space to the breathing in space, pass through the filter pad and the induction valve 1, and is led to the mask.

In above mentioned Example, the seat of inhalation valve is formed as concave groove shape of semicircular cross sectional view. However, occasionally, the seat can be formed as concave groove shape of V figure or square, and the film valve body can be attached likely U figure. Or, the seat can be formed as concave bowl shape, and the bowl shaped film valve body can be attached to the said seat.

By using the present invention the following effects can be obtained.

(1) According to the present invention, an inhalation valve which can act by remarkably lower breathing-in pressure compared to the conventionally well-known inhalation valve. That is, the inhalation resistance of the inhalation valve is estimated by the condition of an air flow rate of 40 litter/minute. According to the result, the inhalation resistance of the conventional inhalation valve which uses rubber thin film valve body is about 1.5 mmH$_2$O, and that of the inhalation valve of this invention is about 0.7 mmH$_2$O. It is clearly understood that the breathing resistance of this invention is below ½ level of that of conventional one.

(2) By applying this invention, a mask of which inhalation resistance is remarkably lower than that of conventionally well-known mask can be obtained.

Figure 8:
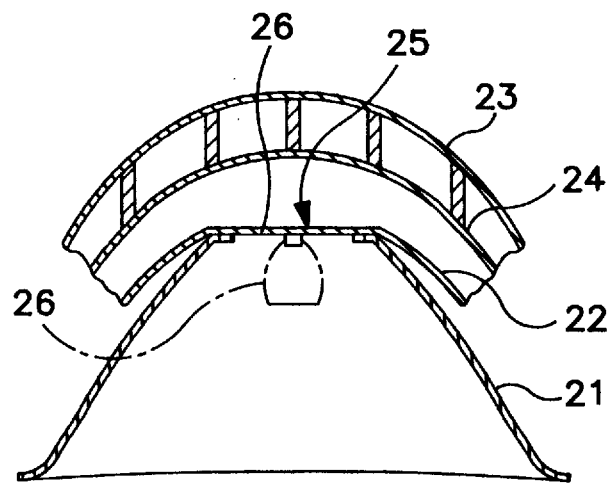
FIG. 8 A schematic illustration of main part of conventionally well-known mask

(3) In the case of conventionally well-known mask, as indicated in FIG. 8 by dotted line, a round thin film valve body 26 rises by itself in the face contact portion when the inhalation valve is opened, while in the case of a mask of this invention, since it is clearly understood by FIG. 7 and FIG. 3 that the whole inhalation valve is embedded in the breathing-in space and the valve body dose not enter into the face contact portion 11, the face contact portion can be arranged more closely to the face, therefore the mask having a wider range of view can be obtained.

While the preferred form of the present invention has been described, it is to be understood that modifications will be apparent to those skilled in the art without departing from the spirit of the invention.

The scope of the invention, therefore, is to be determined solely by the following claims.

What is claim is:

1. An inhalation valve comprising:
    a valve seat comprising:
        a planar member having a first side and a second side and an aperture formed therethrough from said first side to said second side,
        a plurality of ribs, attached to said second side of said planar member and spanning said aperture, said plurality of ribs defining a surface of concave shape coextensive with said aperture;
    and
    a valve body comprising:
        a film having a shape congruent with said concave shape defined by said plurality of ribs, said film being supportable by said plurality of ribs and attached to at least a portion of one of said ribs;
    whereby, in operation, application of gas pressure on said first side of said planar member will force said film into contact with said plurality of ribs and close said aperture to the passage of gas therethrough, and, application of gas pressure on said second side of said planar member will force said film away from said plurality or ribs and open said aperture to the passage of gas therethrough.

2. The inhalation valve of claim 1, wherein said aperture formed through said planar member has a first end, a second end and a pair of substantially parallel sides connecting said first and second end; and said valve seat further comprises:
    a first end wall, proximate said first end of said aperture, formed on said second side of said planar member and extending outwardly therefrom, and
    a second end wall, proximate said second end of said aperture, formed on said second side of said planar member and extending outwardly therefrom.

3. The inhalation valve of claim 2, further comprising a backbone member connecting said first end wall and said second end wall, said plurality of ribs being disposed transversely to said backbone member and connected thereto, said film being attached to at least a portion of said backbone member.

4. The inhalation valve of claim 3, further comprising:
    a first float prevent member, attached to said first end wall and extending over said aperture, said first float prevent member being disposed beneath said backbone member, a portion of said film being receivable between said backbone member and said first float prevent member, and
    a second float prevent member, attached to said second end wall and extending over said aperture, said second float prevent member being disposed beneath said backbone member, a portion of said film being receivable between said backbone member and said second float prevent member.

5. An inhalation valve comprising:
    a valve seat comprising:
        a planar member having a first side and a second side and an aperture formed therethrough from said first side to said second side,
        a plurality of ribs, attached to said second side of said planar member and spanning said aperture, said plurality of ribs defining a surface of concave shape coextensive with said aperture;
    and
    a valve body comprising:
        a film having a shape congruent with said concave shape defined by said plurality of ribs, said film being supportable by said plurality of ribs and attached to at least a portion of one of said ribs, said film having a self recovering force holding said film closely to said concave shape defined by said plurality of ribs, said film having a thickness of 20–80 microns;
    whereby, in operation, application of gas pressure on said first side of said planar member will force said film into contact with said plurality of ribs and close said aperture to the passage of gas therethrough, and, application of gas pressure on said second side of said planar member will force said film away from said plurality or ribs and open said aperture to the passage of gas therethrough.

6. The inhalation valve of claim 5, wherein said aperture formed through said planar member has a first end, a second end and a pair of substantially parallel sides connecting said first and second end; and said valve seat further comprises:

- a first end wall, proximate said first end of said aperture, formed on said second side of said planar member and extending outwardly therefrom, and
- a second end wall, proximate said second end of said aperture, formed on said second side of said planar member and extending outwardly therefrom.

7. The inhalation valve of claim 6, further comprising a backbone member connecting said first end wall and said second end wall, said plurality of ribs being disposed transversely to said backbone member and connected thereto, said film being attached to at least a portion of said backbone member.

8. The inhalation valve of claim 7, further comprising:

- a first float prevent member, attached to said first end wall and extending over said aperture, said first float prevent member being disposed beneath said backbone member, a portion of said film being receivable between said backbone member and said first float prevent member, and
- a second float prevent member, attached to said second end wall and extending over said aperture, said second float prevent member being disposed beneath said backbone member, a portion of said film being receivable between said backbone member and said second float prevent member.

* * * * *